United States Patent [19]

Evans et al.

[11] Patent Number: 4,885,237

[45] Date of Patent: Dec. 5, 1989

[54] DETECTION OF CELLULAR DNA

[75] Inventors: Elizabeth L. Evans, Saratoga, Calif.; Nick J. Gonchoroff; Philip R. Greipp, both of Rochester, Minn.; David W. Houck, Mountain View, Calif.; Jerry A. Katzmann; Robert A. Kyle, both of Rochester, Minn.; Michael R. Loken, Los Altos, Calif.

[73] Assignee: Becton, Dickinson and Company, Franklin Lakes, N.J.

[21] Appl. No.: 205,013

[22] Filed: Jun. 6, 1988

Related U.S. Application Data

[63] Continuation of Ser. No. 798,506, Nov. 15, 1985, abandoned.

[51] Int. Cl.[4] .................. C12Q 1/68; G01N 33/00
[52] U.S. Cl. .................................. 435/6; 435/7; 435/172.2; 435/810; 436/501; 436/508; 436/531; 436/548; 436/822; 530/388; 530/808

[58] Field of Search ............ 435/6, 7, 68, 172.2, 435/810; 436/501, 508, 531, 548, 822; 530/388, 808

[56] References Cited

U.S. PATENT DOCUMENTS

| | | | |
|---|---|---|---|
| 4,381,292 | 4/1983 | Bieber et al. | 436/548 X |
| 4,446,122 | 5/1984 | Chu et al. | 436/548 X |
| 4,529,700 | 6/1985 | Gratzner | 436/548 X |
| 4,585,736 | 4/1986 | Dolbeare et al. | 435/6 |

Primary Examiner—Robert J. Warden
Assistant Examiner—Richard Wagner
Attorney, Agent, or Firm—Robert M. Hallenbeck

[57] ABSTRACT

A method is described for the detection of halodeoxyuridines taken up by cells during DNA synthesis by the use of monoclonal antibodies. The described method also allows the simultaneous detection of cell surface receptors.

35 Claims, 5 Drawing Sheets

DETECTION OF CELLULAR DNA

This application is a continuation of application Ser. No. 798,506, filed Nov. 15, 1985 now abandoned.

FIELD OF THE INVENTION

The present invention relates to a procedure and materials for measuring DNA synthesis. More particularly, the present invention relates to a method for the detection of halodeoxyuridine taken up by cells during DNA synthesis simultaneously with the detection of cell surface receptors. The present invention is particularly suitable for use in flow cytometry apparatus and in transmission or fluorescent microscopy.

BACKGROUND OF THE INVENTION

In living cells, prior to cell division, DNA is duplicated by synthesizing a new daughter strand of DNA from the four nucleic acids, cytidine, thymidine, adenosine and guanosine. The daughter strand is a complementary copy of the parent strand of DNA. The period during the cell cycle in which the new DNA strand is synthesized is called the "S-Phase". During DNA synthesis or repair, in any phase, including the S-Phase, cells take up nucleic acids from their environment and insert them into the newly synthesized DNA. Through use of labelled nucleic acids, it is possible to identify those cells which are taking up nucleic acids from the environment and to identify such cells, including S-Phase cells. One of the most commonly used labelled nucleic acids is tritiated Thymidine.

Another known and commonly used label is bromodeoxyuridine (BrdU) which is an analog of the natural nucleic acid thymidine.

Once one of the labelled nucleic acids is incorporated in the cell which is undergoing DNA synthesis, its presence in the cell can be detected in order to identify such cells. Detection of the tritium label can be done with either liquid scintillation counting or by autoradiography, as described by Taylor, et al., Proc. Natl. Acad. Sci., USA 43:122(1957) and R. Baserga and D. Malamud. Autoradiograph: Technique and Application, Harper, New York (1969). Both methods detect the emitted beta radiation of the tritium label.

The process of autoradiography involves overlaying a microscope slide, firstly with cells having the tritium label incorporated in them and secondly with a photographic emulsion. The emulsion-bearing slide is stored for a time sufficient to expose the emulsion to particles emitted from the decaying tritium in the cells; this period usually takes several days and may last as long as several weeks. The slide is photographically developed revealing fogging of the emulsion which is caused by radiation issued from the decaying tritium. This radiation causes the emulsion to be visible over only those cells which have been incorporating the tritiated thymidine into their DNA. The proportion of DNA-synthesizing cells in the total population can then be enumerated by use of a microscope. Approximate quantitation of the amount of radioactive DNA synthesized per cell can be estimated by counting the silver grains from the emulsion overlying each cell.

In the case of liquid scintillation, a population of cells, approximately 10,000, must be counted so that studies of individual cells become impossible. This approach provides information on the average behavior of a group of cells but does not permit single cell analysis.

The process of DNA synthesis can also be determined by the use of halodeoxyuridine (halodu). Since these compounds appear to the cell as thymidine, they are usually incorporated into DNA in place of thymidine. Thus, the synthesis of DNA by the cell can be monitored by measuring in some manner the incorporation of halodeoxyuridine. Recently, a method for the detection of BrdU incorporation into cells which are synthesizing DNA using polyclonal antibodies has been reported; H. G. Gratzner, et al., J. Histochem. Cytochem., 24, 34 (1976); H. G. Gratzner, et al., Res. Comm. Chem. Pathol. Pharmacol., 20, 34 (1978). Also, U.S. Pat. No. 4,529,700 of Gratzner discloses the development of hybridomas that produce monoclonal antibodies to halodu; i.e., to BrdU, Idu, Cldu and Fldu. A monoclonal antibody to halodu can be tagged with a marker which can be detected in a flow cytometry apparatus or by transmission or fluorescent microscopy. The usual marker for flow cytometry is a fluorescent marker.

Unfortunately, all of the methods utilizing antibodies to halodu for the detection of cells synthesizing DNA have relied upon the destruction of the cell membrane and denaturation of double stranded DNA to single stranded DNA prior to the examination of the DNA. The method for denaturation of DNA is usually incubation with a strong inorganic acid, such as hydrochloric acid, or a base, such as sodium hydroxide. This also results in the breaking down of the DNA from double-stranded DNA into single-stranded DNA and destruction of cellular morphology and cellular antigens.

It would be desirable to provide a method for the detection of newly synthesized DNA in cells without exposure of the cells to harsh acidic or basic conditions. Such method would provide a means whereby the newly synthesized DNA can be detected and quantified while at the same time antigenic determinants on the surface of the cell can be detected. This would result in a greatly simplified method for a complete analysis of the cell to determine cell surface markers, such as those recognized by the anti-Leu series of monoclonal antibodies commercially available from the Becton Dickinson Monoclonal Center, Mountain View, Calif., while at the same time detecting and quantifying newly synthesized DNA.

The detection of cells which have newly synthesized DNA as part of their proliferation cycles is highly desirable in the course of monitoring cell growth of normal and tumor cells; the effects of drugs on DNA proliferation during human cancer therapy; improved detection of chemicals which are potentially damaging to DNA to provide a more sensitive method for facilitating the monitoring of human cells for evidence of genetic injury; and as a tool to measure hypoxanthine phosphoribosyl transferase (HPRT) deficiency in human cells.

SUMMARY OF THE INVENTION

Accordingly, it is an object of the present invention to provide a method for the detection of those cells which have newly synthesized DNA without destroying cellular antigens on those cells in which the newly synthesized DNA has occurred.

It is another object of the present invention to provide a method for utilizing monoclonal antibodies to halodu incorporated into newly synthesized DNA without destroying the cell morphology and antigens prior to binding the monoclonal antibody to the halodu.

Another object of the invention is to provide a kit utilizing monoclonal antibodies for use in the detection of halodu in cellular DNA or RNA.

A further object of the invention is to provide a method for the simultaneous detection of cell surface antigens and newly synthesized DNA within the nucleus of the cell.

To achieve the foregoing and other objects, the present invention is directed to a method for detecting newly synthesized DNA wherein halodu is incorporated into the newly synthesized DNA by binding a monoclonal antibody to the incorporated halodu in the presence of an enzyme which exposes the DNA to the monoclonal antibody.

DETAILED DESCRIPTION OF THE INVENTION

In accordance with the method of the invention, viable cells are contacted with halodu either in vivo or in vitro. The preferred halodu is BrdU and further discussion in the present application will, at times, be based upon the use of BrdU. It should be understood, however, that other halodu reagents can be used. The viable cells may be obtained from any suitable source, such as peripheral blood, solid tissue, tissue culture cells or bone marrow. In most cases, the method is used for the investigation of viable human cells, although other sources of viable cells can be utilized.

The viable cells are preferably contacted with BrdU in a growth media for a period of time sufficient to permit those cells which are synthesizing DNA to incorporate the BrdU into the newly synthesized DNA. Alternatively, the cells can be contacted with Brdu by in vivo administration of Brdu. In most cases, the period of time in which the cells remain in contact with BrdU is from about 15 minutes to 24 hours. The incubation of cells with BrdU may take place in the presence of other chemicals, such as chemotherapeutic agents. After the cells have been contacted with BrdU for a sufficient period of time, other cellular antigens, particularly those on the surface of the cells are tagged with any desirable and suitable cell surface marker. The cell surface markers are usually monoclonal antibodies reactive with various cell surface antigens which have been conjugated to a suitable fluorescent compound. There is ample literature which describes the conjugation of a wide variety of compounds to proteins, such as monoclonal antibodies.

Fluorescein, a widely used fluorescent compound, is a useful emitter in the green region. U.S. Pat. No. 4,520,110 to Stryer describes fluorescent substances that emit in the longer wave length visible region (yellow to red). Multiple fluorescent compounds can be utilized if their spectral properties allow them to be detected independently.

After the cell surface antigens have been tagged with a suitable and desired monoclonal antibody cell surface marker or markers, the cells which have now been contacted with BrdU and with the desired monoclonal antibody cell surface markers, are fixed to preserve the cell structure and to provide openings in the cell membrane. Processes that can be used to fix the cells are well known. In one procedure the cells are resuspended in cold 70% ethanol for 30 minutes. Other fixatives may be used, however, it is necessary for the process to provide openings in the cell membrane for the passage of the anti-BrdU monoclonal antibodies to the nucleus without destroying or making unavailable the cell surface antigens which have been tagged with other monoclonal antibody markers. Cytoplasmic antigens can also be tagged with monoclonal antibodies at this time.

The nuclear material within the cell is then contacted with an enzyme. The enzyme may be a purified enzyme or the enzyme may be in a crude mixture provided by a microorganism. The enzyme is preferably a nuclease or any enzyme with substantial nuclease activity. A suitable nuclease is DNAse 1, from bovine pancreas. The nuclease is added to the cells at a level of from about 0.035 to about 100 units, preferably from about 0.05 to about 50 units.

As indicated, the enzyme may be provided by a microorganism. A suitable microorganism has been found to be *Mycoplasma fermentans*.

While not wishing to be bound by any theory, it is believed that the enzyme opens the double-stranded DNA molecule for access by the monoclonal antibody to the incorporated BrdU and that the DNA remains at least partially in a double-stranded form.

The cell is then contacted with a monoclonal antibody for BrdU. The anti-BrdU monoclonal antibody may be any known anti-BrdU monoclonal antibody. In particular, the anti-BrdU monoclonal antibody which has been deposited with the American Type Culture Collection and which is identified as ATCC No. HB 8914. The treatment of the cells with the enzyme and antibody may be sequential as just described. It is also possible to mix the enzyme and antibody solutions so that they may be added together.

The anti-BrdU monoclonal antibody can be conjugated to a suitable marker. In another method, the monoclonal antibody for BrdU can be detected in an indirect manner. In the indirect method the anti-BrdU monoclonal antibody does not carry a dye but is identified by a second antibody which bears a detectable label. The label can be a fluorescent dye or an enzyme, such as alkaline phosphatase. The fluorescent markers described in U.S. Pat. No. 4,520,110 are particularly suitable for use as a fluorescent marker for the anti-BrdU monoclonal antibody. The anti-BrdU monoclonal antibody is added at a level sufficient to mark the BrdU molecules which have been incorporated into the newly synthesized DNA. In general, a level of from about 0.1 to about 100 micrograms per $10^6$ cells has been found to be suitable.

The cells which have been marked with cell surface or cytoplasmic markers and with the anti-BrdU monoclonal antibody are now ready to be analyzed by fluorescent microscopy or by passage through a flow cytometry apparatus. In general, the fluorescent signal provided by each of the fluorescent markers is separately distinguished and the data provided by the detection of the fluorescent signal is recorded in a suitable device, such as a computer.

The following examples further illustrate various features of the invention but are intended to in no way limit the scope of the invention which is defined in the appended claims.

The following examples make reference to several Figures in which.

EXAMPLES

EXAMPLE 1

Hapten inhibition of anti-BrdU monoclonal antibody.

Figure 1:
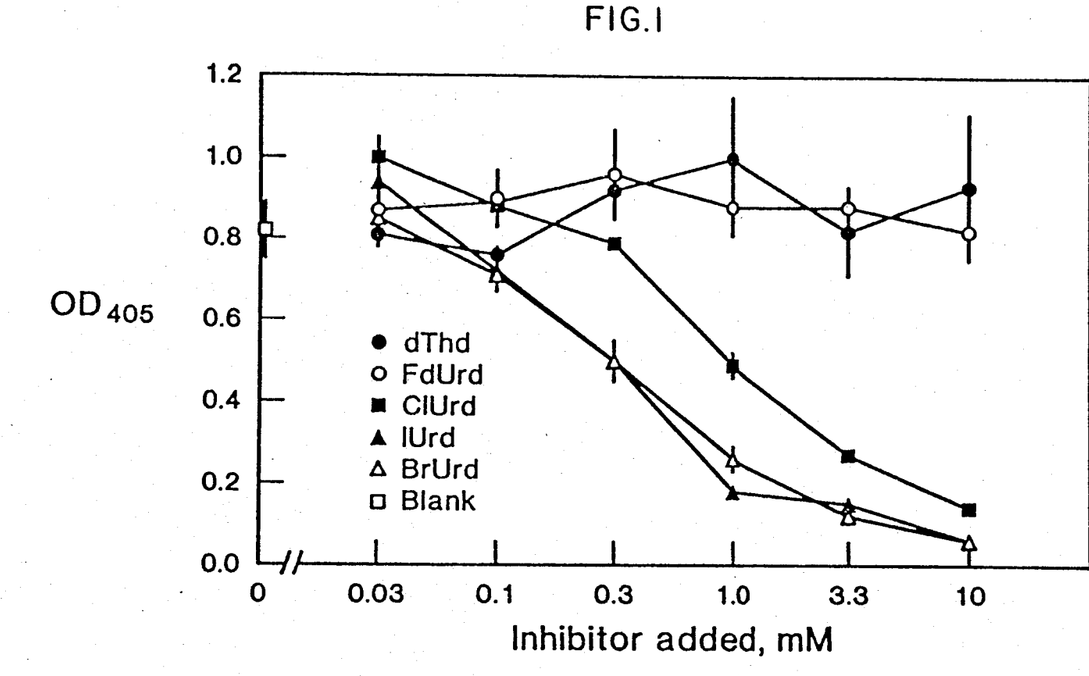
FIG. 1 is a plot of the specificity of BU-1 antibody to various halodus as measured by optical density.

As shown in FIG. 1, six different concentrations of either thymidine, 5-bromo-2-deoxyuridine, 5-fluoro-2-deoxyuridine, 5-iodo-2-deoxyuridiee, or 5-chloro-2-deoxyuridine, were each added to 300 ng of a cell culture supernatant produced from ATCC # HB 8914 containing a monoclonal antibody to halodu (referred to hereinafter as BU-1 antibody) and incubated for 30 min at 37° C. This mixture was then added to a microtiter well containing bound iodouridine/ovalbumin antigen and incubated for 30 min at room temperature. The plate was washed 4x and the bound monoclonal antibody was detected by addition of 160 ng of goat anti-mouse alkaline phosphatase conjugate. After 30 min incubation the unbound conjugate was removed by washing and bound conjugate was detected by the addition of p-nitrophenyl phosphate. At 20 min the reaction was stopped with 3M NaOH and the optical density (OD) was read in a microtiter plate reader. Error bars given are for one standard deviation from a triplicate determination. The data shown in FIG. 1 indicates that thymidine and Fdu do not inhibit binding of the monoclonal antibody, whereas BrdU, Cldu and Idu do inhibit binding.

EXAMPLE 2

Cells in mitosis stained with BU-1 antibody. Lymphocytes from a normal donor were incubated for 72 hrs in RPMI 1640 supplemented with PHA. BrdU was added during the final 6 hrs and treated with colcemid for 1 hr prior to being harvested. BU-1 antibody containing nuclease from *Mycoplasma fermentans* was added. The bound antibody was detected using fluorescent microscopy by the addition of FITC-labeled goat anti-mouse IgG conjugate. Control slides with the monoclonal antibody or conjugate alone were negative.

EXAMPLE 3

Immunocytochemical assay. One million human bone marrow cells were incubated for 1 hr in BrdU and FdU containing media. Slides were made, fixed and BU-1 antibody in the presence of *Mycoplasma fermentans* was added. The bound BU-1 antibody was detected by a goat anti-mouse alkaline phosphatase conjugate. The alkaline phosphatase was detected by napthol AS phosphate as a substrate. The nucleus of positive cells are a bright red, which upon being photographed with black and white film, appear dark.

EXAMPLE 4

Figure 2:
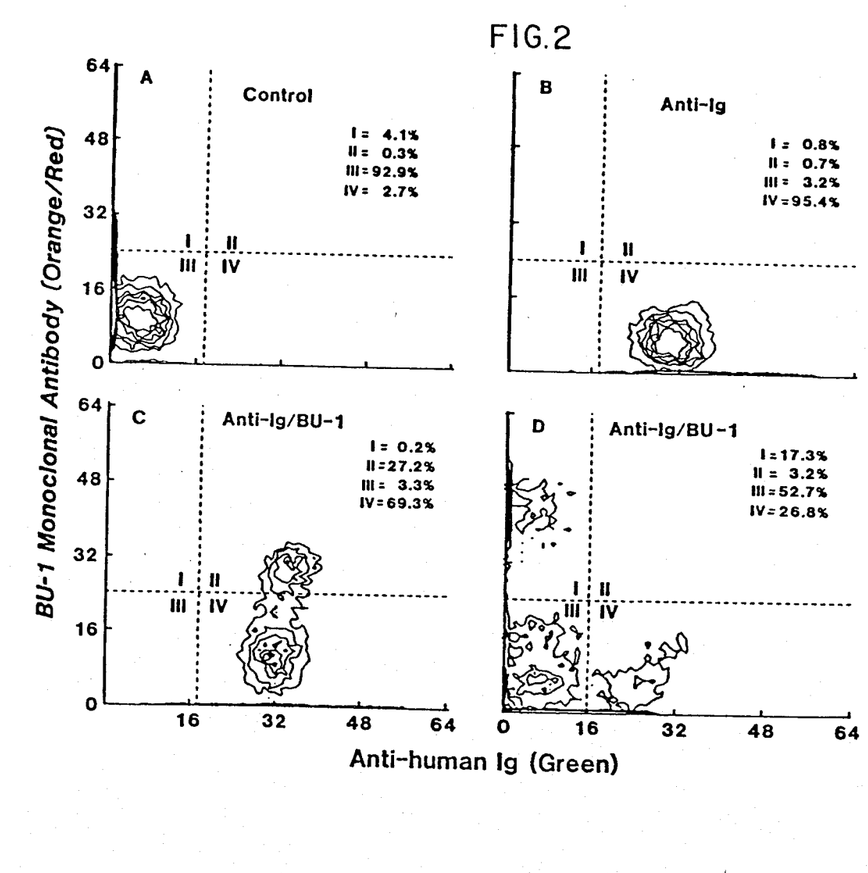
FIG. 2 is a contour plot of fluorescence for human myeloma cells incubated with BrdU and FdU upon exposure to labeled BU-1 antibody and propidium iodide and to propidium iodide as a control.

Double staining with BU-1 and Propidian Iodide (PI). One million cells of a human myeloma cell line were incubated for 1 hr in the presence of BrdU and FdU. They were then washed 2x with 0.15M NaCL and resuspended in 3 ml of cold 0.15M NaCL and 9 ml of cold ethanol was added. After 30 min incubation at room temperature, the cells were washed and treated with RNase for 30 min at 37° C. The cells were then stained with BU-1 in the presence of *Mycoplasma fermentans* and goat anti-mouse FITC conjugate. After washing, the cells were resuspended in 10 ug/ml PI and analyzed on a FACS IV using the 488 nm wavelength for excitation. The results are shown in FIG. 2.

EXAMPLE 5

Figure 3:
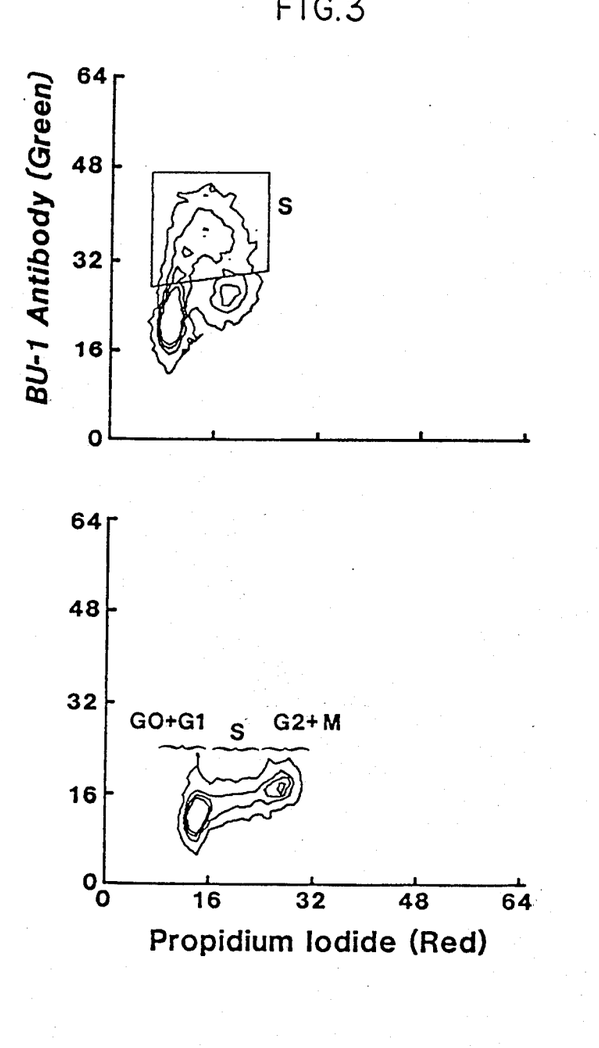
FIG. 3 comprises four contour plots of fluorescence for human myeloma cells (a)–(C) and human multiple myeloma bone marrow cells (D) incubated with BrdU and FdU when reacted with labeled BU-1 antibody and anti-human Ig.

Double staining with BU-1 and anti-human Ig. One million human myeloma or human bone marrow cells were incubated 1 hr in the presence of BrdU and FdU. They were then washed with 0.15M NaCL and resuspended in 3 ml of 0.15M NaCL and 9 ml of ethanol added. After 30 min incubation at room temperature, the cells were washed once with 1.0% BSA/PBS and resuspended in the same buffer. The cells were then reacted with BU-1 in the presence of *Mycoplasma fermentans* and sheep anti-mouse IgG biotin-labeled antibodies. After washing, the cells were stained with phycoerythrin-labeled avidin and anti-human Ig FITC labeled conjugate. As shown in FIG. 3, Panels: (A) Control; (B) human myeloma cells stained with anti-human Ig; (C) human myeloma cells stained with BU-1 antibody (red fluorescence) and anti-human IG antibody (green fluorescence); (D) human multiple myeloma bone marrow cells stained with BU-1 antibody (red fluorescence) and anti-human Ig antibody (green fluorescence). Mapping dots were erased and the contour plots redrawn for clarity.

EXAMPLE 6

Figure 4:
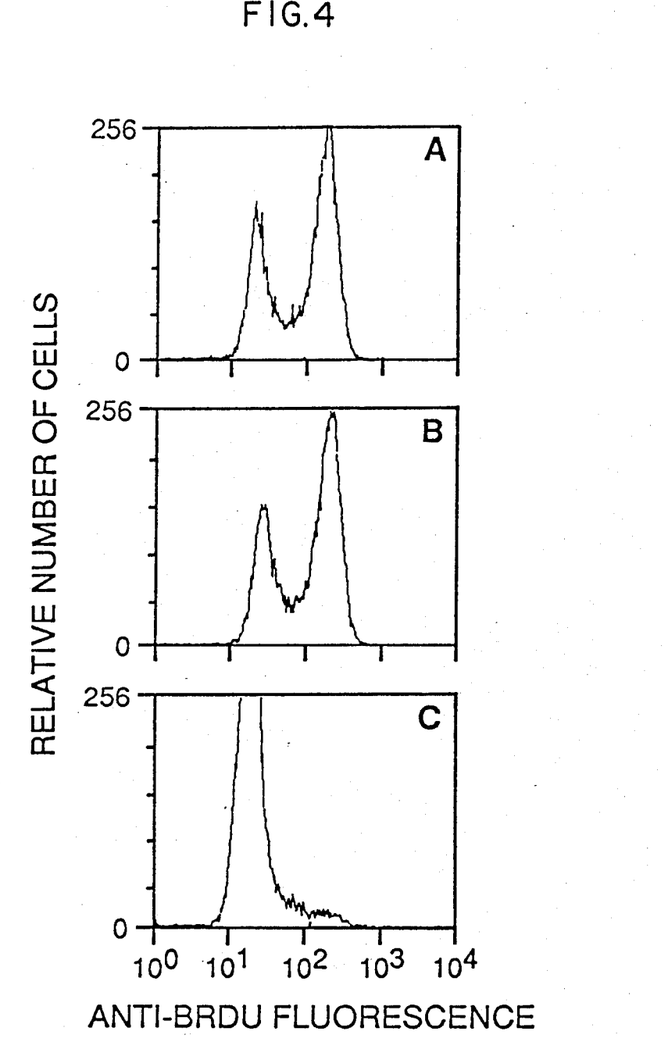
FIG. 4 comprises three histograms for murine tissue culture cells labeled with BrdU when exposed to (A) *Mycoplasma fermentans* and BU-1 antibody sequentially, (B) a mixture of *Mycoplasma fermentans* and BU-1 antibody or (C) to BU-1 antibody alone.

Murine tissue culture cells were labelled with BrdU for 30 minutes. The cells were washed and fixed with 70% ethanol for 30 minutes in the cold. After fixation the cells were washed twice with phosphate buffered saline and exposed to (A) a supernatant from a cell line containing with *Mycoplasma fermentans* and then to the BU-1 antibody sequentially; (B) a supernatant from a cell line containing *Mycoplasma fermentans* and the BU-1 antibody simultaneously or (C) to BU-1 antibody alone. All three samples were then stained with fluorescein conjugated goat anti-mouse immunoglobulin and analyzed on a flow cytometer. The staining seen in both 4A and 4B of FIG. 4 requires the presence of *Mycoplasma fermentans* either before or at the same time as exposure to the BU-1 antibody. No staining was observed with no added supernatant as shown in FIG. 4 (C).

EXAMPLE 7

Figure 5:
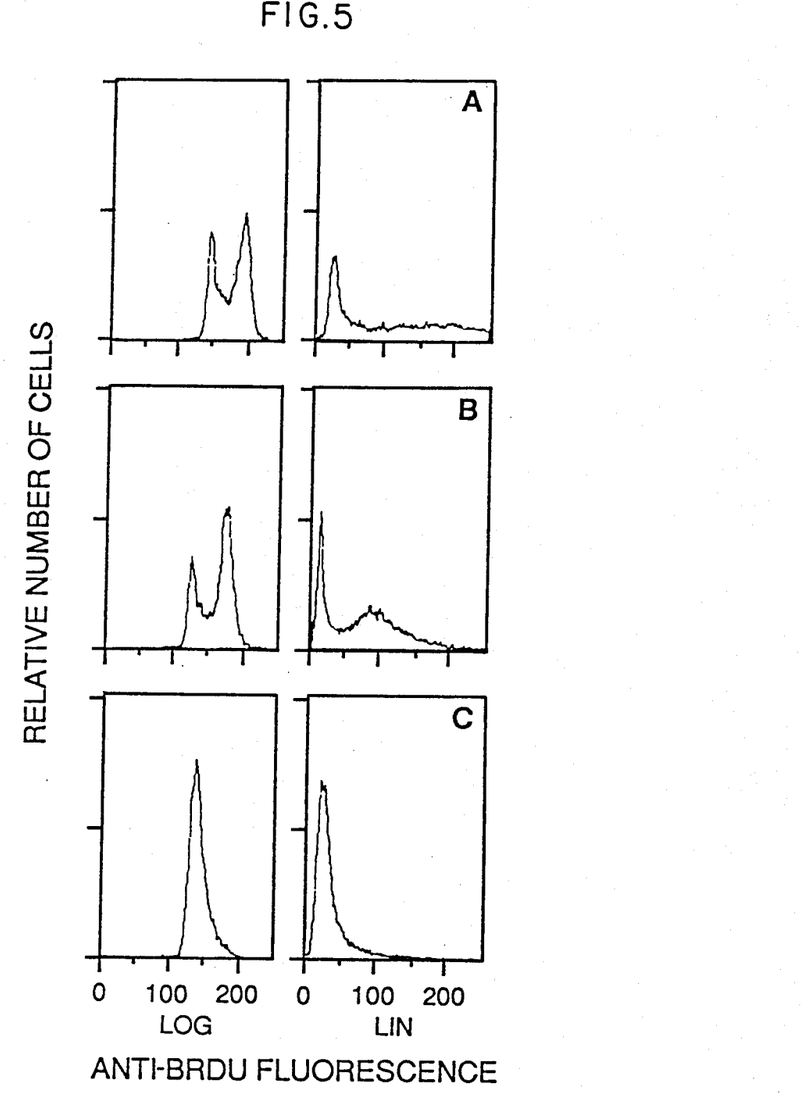
FIG. 5 comprises three histograms for murine tissue culture cells labeled with BrdU upon exposure to varying amounts of DNase and BU-1 antibody.

Murine tissue culture cells were labelled with BrdU for 30 minutes. The cells were washed and fixed with 70% ethanol for 30 minutes in the cold. After fixation the cells were washed twice with phosphate buffered saline and exposed to varying concentrations of DNAse I isolated from bovine pancreas. After treating with the enzyme the cells were exposed to the BU-1 antibody followed by a second step of fluorescein labelled goat anti-mouse immunoglobulin. FIG. 5 compares the fluorescence as assayed on a flow cytometer, (A) 100 units, DNAse I, (B) 3.12 units, DNAse I, (C) no DNAse I.

The foregoing description of the preferred embodiments of the present invention have been presented for purposes of illustration and description and for a better understanding of the invention. The description is not intended to be exhaustive or to limit the invention to the precise form disclosed. Obviously, many modifications are possible in view of the teaching of the present invention. The particular embodiments were chosen and described so as to best explain the principles of the invention and its practical application to enable those skilled in the relevant art to best utilized the invention as suited to the particular use contemplated.

What is claimed is:

1. A method for detecting halodu which has been incorporated into double-stranded DNA of a cell comprising the steps of treating the cell with a fixative that will partially disrupt the plasma membrane to allow passage of monoclonal antibodies to the cell nucleus, then contacting the DNA within the cell with an enzyme, wherein said enzyme will partially disrupt the hydrogen bonds between the double-stranded DNA, then exposing the treated DNA to an anti-halodu monoclonal antibody and then detecting the halodu which is bound by the anti-halodu antibody, wherein halodu is selected from the group consisting of BrdU, IdU and CldU.

2. A method in accordance with claim 1 wherein the halodu is BrdU.

3. A method in accordance with claim 1 wherein the halodu is IdU.

4. A method in accordance with claim 1 wherein the anti-halodu monoclonal antibody is the monoclonal antibody produced by the hybridoma identified as ATCC Number HB 8914.

5. A method in accordance with claim 1 wherein said enzyme is a nuclease.

6. A method in accordance with claim 5 wherein said nuclease is a purified nuclease.

7. A method in accordance with claim 5 wherein said nuclease is provided by a microorganism.

8. A method in accordance with claim 7 wherein said microorganism is *Mycoplasma fermentans*.

9. A method for simultaneous detection of a cellular antigen and double-stranded DNA synthesized within a cell comprising the steps of providing a sample of viable cells, exposing said viable cells to halodu so as to provide synthesized, double-stranded DNA having a halodu incorporated therein, wherein halodu is selected from the group consisting of BrdU, IdU and CldU, then exposing said cells to a first monoclonal antibody which has specificity to said cellular antigen, then treating the cells with a fixative that will partially disrupt the plasma membrane to allow passage of anti-halodu monoclonal antibodies to the cell nucleus without disrupting the cellular antigens which have been tagged by the first monoclonal antibody, then exposing the DNA within the cell to an enzyme, wherein said enzyme will partially disrupt the hydrogen bonds between the double-stranded DNA, then exposing the enzyme treated DNA to an anti-halodu monoclonal antibody and thereafter detecting the cellular antigen bound to first monoclonal antibody and halodu bound to said anti-halodu monoclonal antibody.

10. A method in accordance with claim 9 wherein at least one of said first monoclonal antibody and said anti-halodu monoclonal antibody is conjugated to a fluorescent marker prior to use.

11. A method in accordance with claim 9 wherein at least one of said first monoclonal antibody and said anti-halodu monoclonal antibody is contacted with an immunoreactive material which is capable of binding with said antibody and which has been coupled to a fluorescent marker prior to said detection step.

12. A method in accordance with claim 9 wherein said detection is effected by passing said exposed sample through a flow cytometer.

13. A method in accordance with claim 9 wherein said detection is effected by transmission or fluorescence microscopes.

14. A method in accordance with claim 9 wherein said cellular antigen is a cell surface antigen.

15. A method in accordance with claim 9 where said cellular antigen is a cytoplasmic antigen.

16. A method in accordance with claim 9 wherein said halodu is BrdU.

17. A method in accordance with claim 9 wherein said halodu is IdU.

18. A method in accordance with claim 9 wherein the anti-halodu monoclonal antibody is the monoclonal antibody produced by the hybridoma identified as ATCC Number HB 8914.

19. A method in accordance with claim 9 wherein said enzyme is a nuclease.

20. A method in accordance with claim 19 wherein said nuclease is a purified nuclease.

21. A method in accordance with claim 19 wherein said nuclease is derived from bovine pancreas.

22. A method in accordance with claim 19 wherein said nuclease is provided by a microorganism.

23. A method in accordance with claim 22 wherein said microorganism is *Mycoplasma fermentans*.

24. A diagnostic kit for detection of double-stranded DNA within a cell having halodu incorporated therein, wherein halodu is selected from the group consisting of BrdU, IdU and CldU, comprising the following components:
   (a) an anti-halodu monoclonal antibody; and
   (b) an enzyme capable of partially disrupting the hydrogen bonds between said double-stranded DNA thereby exposing said incorporated halodu to binding with said anti-halodu monoclonal antibody.

25. A diagnostic kit in accordance with claim 24 wherein the anti-halodu monoclonal antibody is the monoclonal antibody produced by the hybridoma identified as ATCC Number HB 8914.

26. A diagnostic kit in accordance with claim 24 wherein said enzyme is a nuclease.

27. A diagnostic kit in accordance with claim 26 wherein said nuclease is a purified nuclease.

28. A diagnostic kit in accordance with claim 26 wherein said nuclease is derived from bovine pancreas.

29. A diagnostic kit in accordance with claim 24 wherein said enzyme is provided by a microorganism.

30. A diagnostic kit in accordance with claim 29 wherein said microorganism is *Mycoplasm fermentans*.

31. A diagnostic kit in accordance with claim 24 wherein said anti-halodu monoclonal antibody and said enzyme are separately contained.

32. A diagnostic kit in accordance with claim 24 wherein said anti-halodu monoclonal antibody and said enzyme are commonly contained.

33. A diagnostic kit in accordance with claim 24 which also includes at least one additional monoclonal antibody which is specific to a cellular antigen.

34. A diagnostic kit in accordance with claim 24 wherein said anti-halodu monoclonal antibody is conjugated to a fluorescent marker.

35. A diagnostic kit in accordance with claim 24 which also includes an immunoreactive material which is capable of binding with said anti-halodu monoclonal antibody and which has been coupled to a fluorescent marker.

* * * * *